United States Patent [19]

Imai

[11] Patent Number: 5,590,434
[45] Date of Patent: Jan. 7, 1997

[54] ELECTRIC TOOTHBRUSH

[75] Inventor: Kiyoshi Imai, Toyama, Japan

[73] Assignee: Kitano Co., Ltd., Toyama, Japan

[21] Appl. No.: 467,880

[22] Filed: Jun. 6, 1995

[30] Foreign Application Priority Data

Jun. 10, 1994 [JP] Japan ................... 6-008519 U
Jul. 1, 1994 [JP] Japan ................... 6-009603 U

[51] Int. Cl.$^6$ ........................... A46B 13/02
[52] U.S. Cl. ........................... 15/22.1
[58] Field of Search ................... 15/22.1, 22.2; 310/81; 601/87

[56] References Cited

U.S. PATENT DOCUMENTS

| | | | |
|---|---|---|---|
| 3,182,345 | 5/1965 | Smith | 15/22.1 |
| 3,370,214 | 2/1968 | Aymar | 15/22.1 |
| 3,685,080 | 8/1972 | Hubaer | 15/22.1 |
| 5,150,492 | 9/1992 | Suroff | 15/22.2 |
| 5,381,576 | 1/1995 | Hwang | 15/22.1 |

FOREIGN PATENT DOCUMENTS

| | | | |
|---|---|---|---|
| 0510940 | 10/1992 | European Pat. Off. | 15/22.1 |
| 3267010 | 11/1991 | Japan | 15/22.1 |
| 0471560 | 6/1969 | Switzerland | 15/22.2 |
| 8001533 | 8/1980 | WIPO | 15/22.1 |

*Primary Examiner*—David Scherbel
*Assistant Examiner*—Randall E. Chin
*Attorney, Agent, or Firm*—Dennison, Meserole, Pollack & Scheiner

[57] ABSTRACT

A cylindrical case body is formed by a front case and a rear case. An eccentric weight is secured to a rotating shaft of a motor mounted in the front case. A connecting shaft is formed on a front end of the front case, and a brush is attached to the front case by engaging with the connecting shaft. A metallic pin is inserted in the connecting shaft, and an O-ring is disposed between the front case and the rear case.

2 Claims, 3 Drawing Sheets

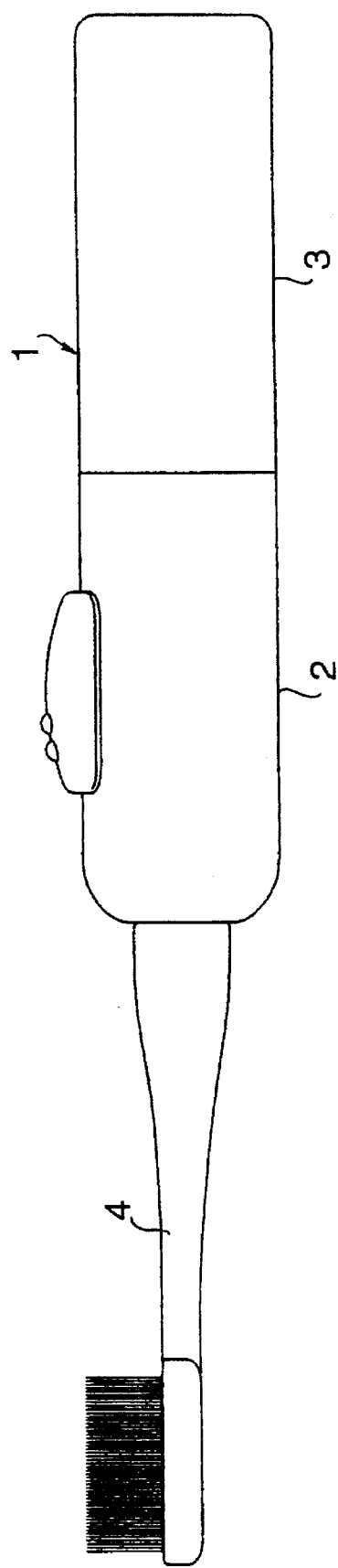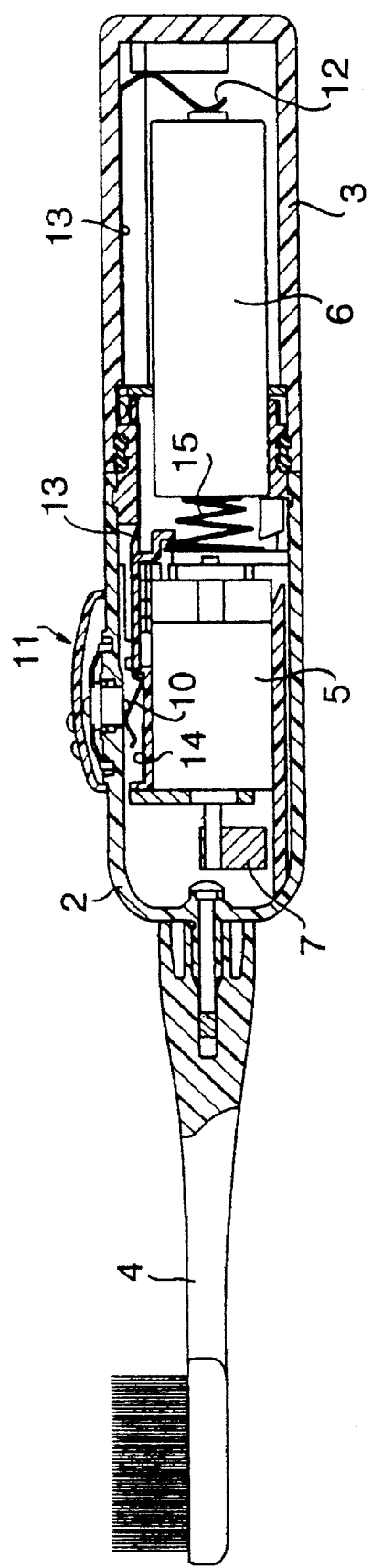

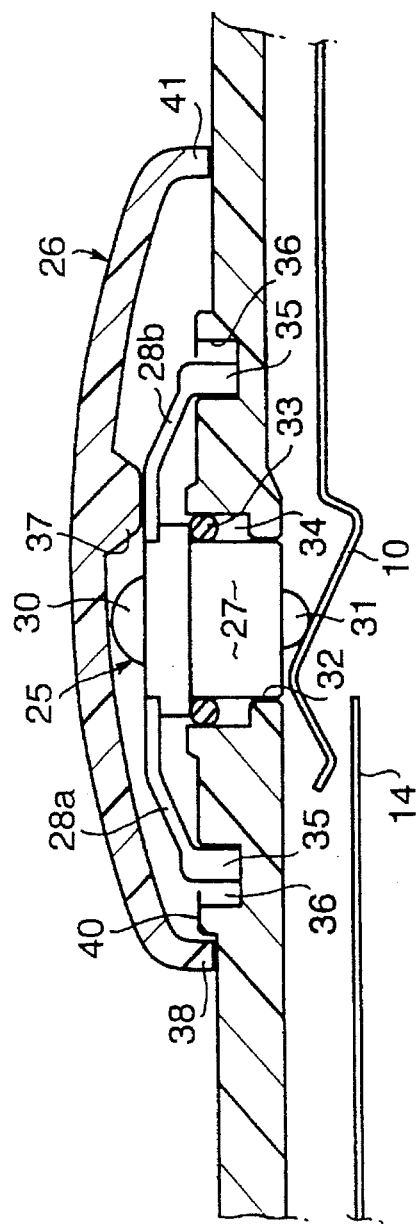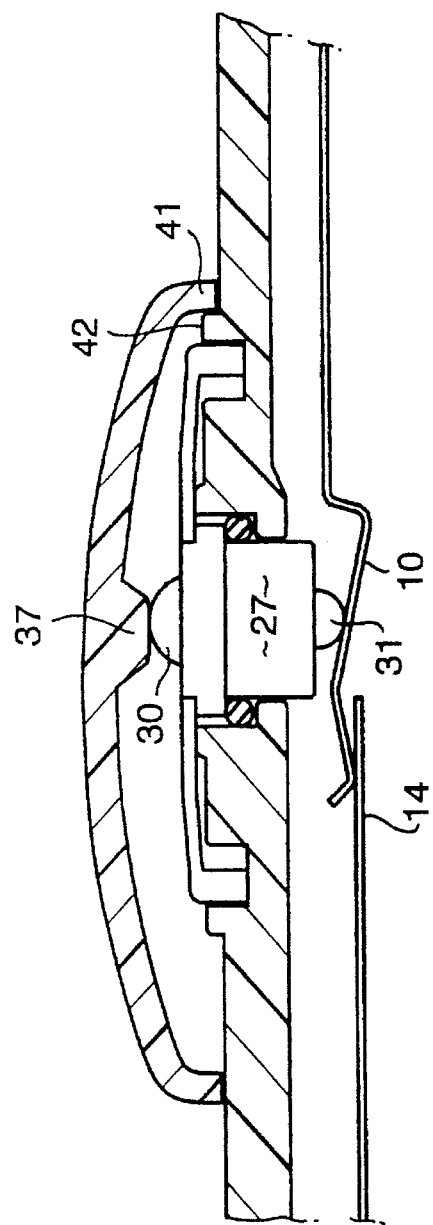

ELECTRIC TOOTHBRUSH

BACKGROUND OF THE INVENTION

The present invention relates to an electric toothbrush.

In general, the electric toothbrush comprises a case body which is divided into a front portion mounting a vibrating device therein and a rear portion as a handle, and a brush portion attached to a front end of the front portion by a connecting shaft projecting from the front end. The front portion is vibrated by the vibrating device, and the vibration is transmitted to the brush portion through the connecting shaft.

The vibration of the front portion is also transmitted to the rear portion as a handle. As a result, the vibration is not effectively transmitted to the brush portion, which means a reduction of vibration efficiency. In addition, the vibration is further transmitted to a hand of a user, thereby giving an unpleasant feeling to the user.

The conventional electric toothbrush has another disadvantage as described below.

the case body is made of plastic and the connecting shaft for attaching the brush portion is integrally formed on the front end of the front portion. When brushing teeth with the electric brush, the brush portion is pressed against teeth and/or gums. Therefore, a lateral force is applied to the connecting shaft through the brush portion. Since the connecting shaft is made of plastic and has a comparatively small diameter, the connecting shaft is liable to be elastically bent to form a gap between the brush portion and the case body. Therefore, the vibration transmitting effect reduces. Furthermore, it happens that the brush portion falls from the case body in an extreme case.

SUMMARY OF THE INVENTION

An object of the present invention is to provide an electric toothbrush in which vibration generated by a vibrating device is effectively transmitted to a brush portion.

According to the present invention, there is provided an electric toothbrush comprising a cylindrical case body comprised of a front case and a rear case, a motor provided in the front case, an eccentric weight secured to a rotating shaft of the motor for generating vibrations, a battery mounted in the rear case for operating the motor, a connecting shaft formed on a front end of the front case, a brush attached to the front case by engaging with the connecting shaft, connecting means for connecting the front case and the rear case with each other, and vibration transmission enhancement means for enhancing vibration transmitting efficiency to the brush.

The vibration transmission enhancement means is a vibration absorbing member such as an O-ring disposed between the front case and the rear case.

The vibration transmission enhancement means may be a metallic pin provided in the connecting shaft.

These and other objects and features of the present invention will become more apparent from the following detailed description with reference to the accompanying drawings.

BRIEF DESCRIPTION OF DRAWINGS

FIG. 1 is a side view showing an electric toothbrush according to the present invention;

FIG. 2 is a sectional view of the electric toothbrush of FIG. 1;

FIGS. 5 and 6 are sectional views showing on on-off switch.

DETAILED DESCRIPTION OF THE PREFERRED EMBODIMENT

Figure 3:
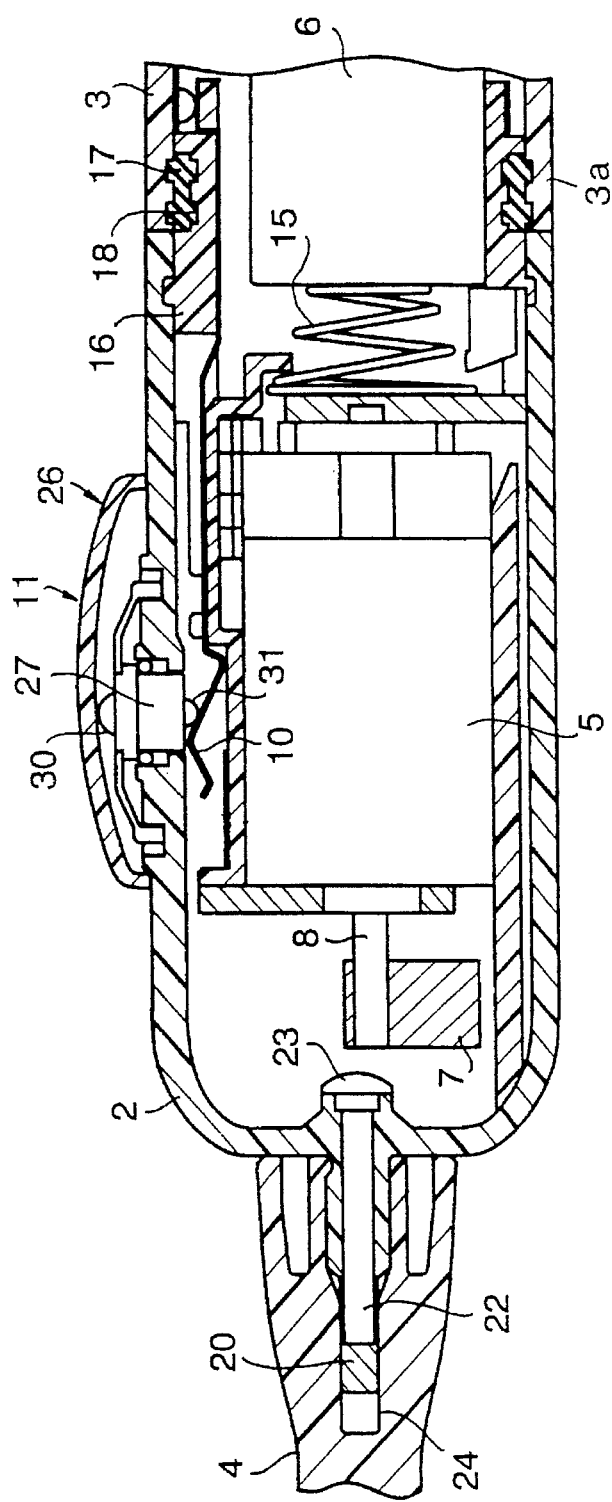
FIG. 3 is an enlarged sectional view of a main part of the electric toothbrush.
Figure 4:
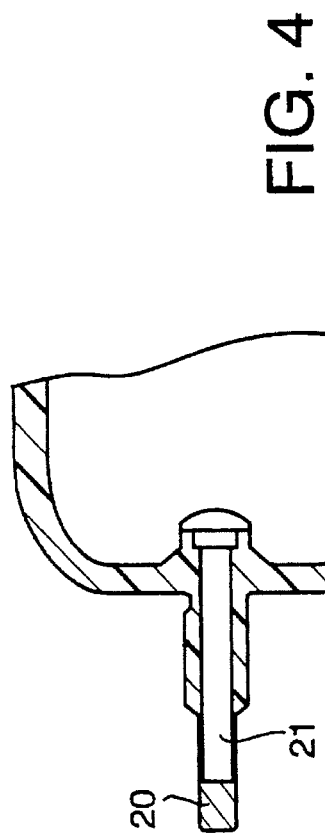
FIG. 4 is an enlarged sectional view of a front part of a case body.

Referring to FIG. 1, the electric toothbrush according to the present invention comprises a cylindrical case body 1 comprised of a front case 2 and a rear case 3 as a handle, and a brush 4 attached to the front case 2.

As shown in FIG. 2, a motor 5 is mounted in the front case 2, and a battery 6 is housed in the rear case 3. An eccentric weight 7 is secured to a rotating shaft 8 of the motor 5. A positive terminal of the battery 6 is connected to a movable contact 10 of an on off switch 11 through a spring plate 12 and a lead 13. A fixed contact 14 of the on-off switch 11 is connected to a positive terminal of the motor 5. A negative terminal of the battery 6 is connected to a negative terminal of the motor 5 through a spring contact 15.

Referring to FIG. 3, a connecting cylinder 16 is secured to the inside wall of the front case 2. The outer diameter of the connecting cylinder 16 is slightly smaller than the inner diameter of the rear case 3 so that the rear case can be engaged on the connecting cylinder. An O-ring 17 is engaged in an annular groove 10 formed on the outside periphery of the connecting cylinder 16. The rear case 3 is connected to the front case 2 by engaging the front portion 30 of the rear case on the connecting cylinder 16, engaged with the O-ring 17 to form a watertight sealing between the front and rear cases.

On the other hand, a connecting shaft 20 is forwardly projected from the front end of the front case 2. In the connecting shaft 20, an axial hole 21 is formed. A metallic pin 22 is engaged in the hole 21 and secured thereto with an adhesive 23.

The brush 4 has an axial hole 24 corresponding to the connecting shaft 20. Thus, the brush 4 is attached to the front case 2 by engaging the hole 24 with the connecting shaft 20.

Referring to FIG. 5, the switch 11 comprises a push button 25 and a slide button 26. The push button 25 is made of plastic and has a shaft portion 27, elastic portions 20a and 20b projecting from the shaft portion 27 in the forward and rearward directions, an upper projection 30 formed on the upper surface of the shaft portion 27, and a lower projecting 31 formed on the underside surface of the shaft portion. The shaft portion 27 is slidably engaged in a lateral hole 32 formed in the front case 2. An O-ring 33 is mounted in an annular space 34 formed between the front case 2 and the shaft portion 27 so that a sealing means is provided for watertightly holding the shaft portion 27. The annular space 34 is formed so as to allow the push button 25 to be moved. Formed on the end of each of the elastic portions 28a and 28b is a leg 35 which is slidably engaged in a hole 36 formed in the front case 2. The lower projection 31 contacts with the movable contact 10 so as to close the switch 11.

The slide button 26 is longitudinally mounted on the front case 2. On the underside of the slide button 26, a pushing projection 37 is formed, corresponding to the upper projection 30. In the unoperated state shown in FIG. 5, a front leg 38 abuts on a front stopper 40.

When the slide button 26 is forwardly slid as shown in FIG. 6, the pushing projection 37 engages with the upper projection 30 to push it, so that the push button 25 is inwardly moved. Thus, the lower projection 31 pushes the movable contact 10 so that the movable contact 10 contacts with the fixed contact 14 to close the switch 11. At that time, a rear leg 41 of the slide button 26 abuts on a rear stopper 42. By the closing of the switch, the motor 5 operates to rotate the eccentric weight 7. Consequently, the front case 2 is vibrated. The vibration of the front case is transmitted to the brush 4 through the connecting shaft 20. On the other hand, since the O-ring 17 is disposed between the front case 2 and the rear case 3, the vibration of the front case is not largely transmitted to the rear case 3. Therefore, the vibration of the front case is effectively transmitted to the brush 4, and the rear case 3 does not largely vibrate. Thus, the toothbrush effectively operates without giving an unpleasant feeling to the user.

Since the metallic pin 22 is inserted in the connecting shaft 20, the shaft is not bent. Therefore, no gap is formed between the brush and the front case. Thus, the vibration of the front case is further effectively transmitted to the brush, and the brush does not drop.

While the invention has been described in conjunction with preferred specific embodiment thereof, it will be understood that this description is intended to illustrate and not limit the scope of the invention, which is defined by the following claims.

What is claimed is:

1. An electric toothbrush comprising:

a cylindrical case body comprised of a front case and a rear case;

the front case having a front end and a rear end with an inside wall;

a motor having a rotating shaft and provided in the front case;

an eccentric weight secured to the rotating shaft of the motor for generating vibrations;

a battery mounted in the rear case for operating the motor;

a connecting shaft integrally formed on the front end of the front case and forwardly projected from the front end, the connecting shaft having an axial hole;

a metallic pin secured in the axial hole of the connecting shaft;

a brush attached to the front case by engaging with the connecting shaft;

a connecting cylinder secured to the inside wall of the rear end of the front case and extending into the rear case; and a vibration absorbing member disposed between the connecting cylinder and the rear case for absorbing the vibration of the eccentric weight.

2. The electric toothbrush according to claim 1 wherein:

the vibration absorbing member is an O-ring disposed between the connecting cylinder and the rear case.

* * * * *

UNITED STATES PATENT AND TRADEMARK OFFICE
CERTIFICATE OF CORRECTION

PATENT NO. : 5,590,434
DATED : January 7, 1997
INVENTOR(S) : KIYOSHI IMAI

It is certified that error appears in the above-indentified patent and that said Letters Patent is hereby corrected as shown below:

Title page:

After [73] Assignee: insert--

Kitano Co., Ltd., Toyama, Japan
Japan CBM Corporation, Tokyo, Japan

Signed and Sealed this

Twenty-third Day of September, 1997

Attest:

BRUCE LEHMAN

Attesting Officer

Commissioner of Patents and Trademarks